United States Patent [19]

Bonne et al.

[11] 4,407,812
[45] Oct. 4, 1983

[54] ETHERAL IMIDAZOLES AND USE IN TREATMENT OF THROMBOSES

[75] Inventors: Claude Bonne, Bry sur Marne; Claude Coquelet, Noisy-le-Roi; Daniel Sincholle, St. Clement, all of France

[73] Assignee: Laboratoires Chauvin-Blache, Montpellier, France

[21] Appl. No.: 226,774

[22] Filed: Jan. 21, 1981

[30] Foreign Application Priority Data

Jan. 31, 1980 [FR] France ............................ 80 02057

[51] Int. Cl.³ ................. C07D 233/54; A61K 31/415
[52] U.S. Cl. ................................ 424/273 R; 548/341
[58] Field of Search .................... 548/341; 424/273 R

[56] References Cited

U.S. PATENT DOCUMENTS 4,285,722 8/1981 Worthington et al. ............ 548/341

OTHER PUBLICATIONS

Tai et al., Biochem. Biophys. Res. Comm., 80, 236–242, 1978.

Pailer et al., Monatshefte für Chemie, 108, 653–664, 1977.

Noller, Textbook of Organic Chemistry, 2nd Ed., W. B. Saunders Co., Philadelphia, 1958, pp. 102, 123.

Primary Examiner—Henry R. Jiles
Assistant Examiner—Robert C. Whittenbaugh
Attorney, Agent, or Firm—Young & Thompson

[57] ABSTRACT

This invention relates to a therapeutic composition comprising, as active ingredient, a compound of the formula (I)

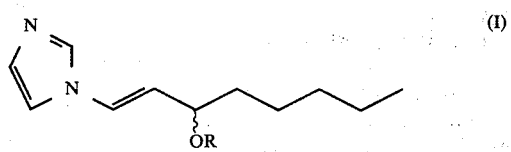

in which R is hydrogen or an ether or ester residue, or a therapeutically acceptable acid addition salt thereof.

This composition is applicable to the treatment and the prevention of thromboses.

11 Claims, 6 Drawing Figures

NE : non enzymatic degradation

FIG. 2 Inhibition of human platelet thromboxane synthetase

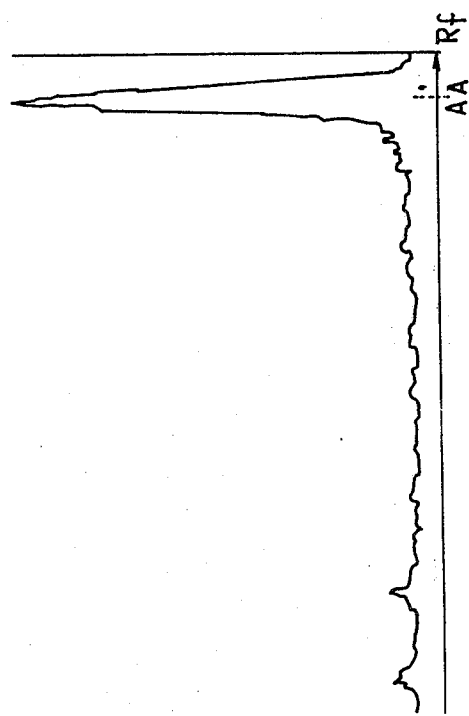
FIG. 4 Aortal microsomes
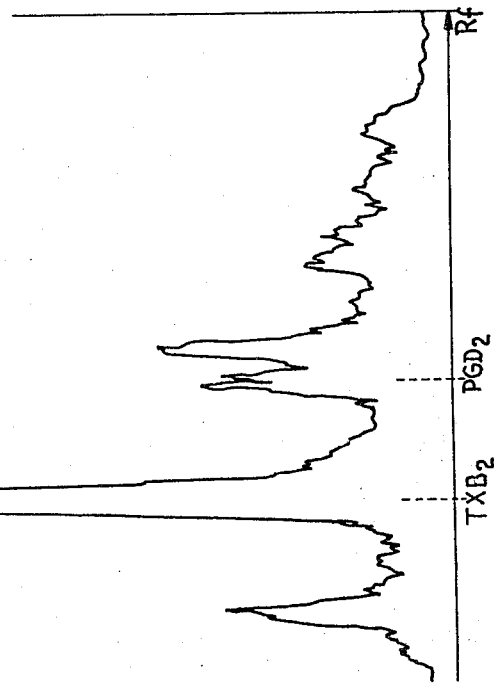
FIG. 3 Platelet suspension

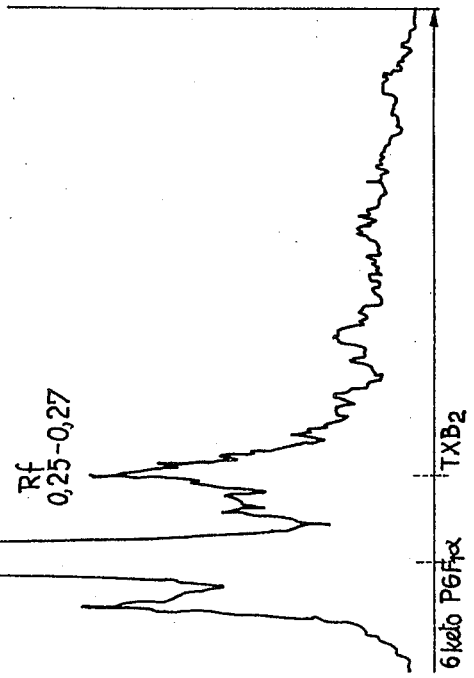
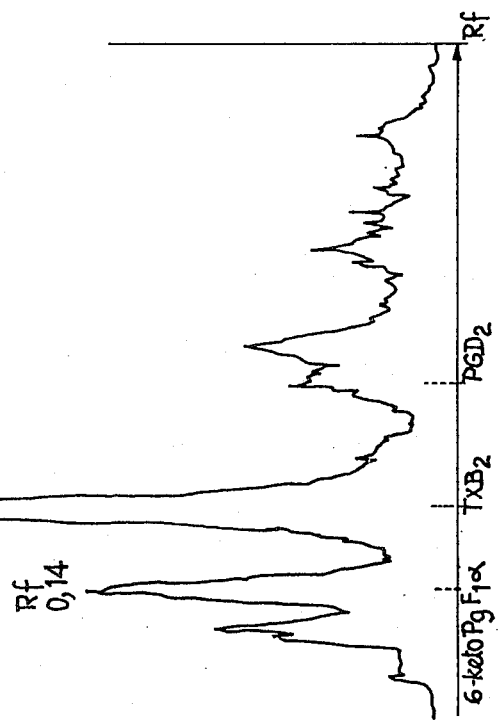

ETHERAL IMIDAZOLES AND USE IN TREATMENT OF THROMBOSES

DESCRIPTION

This invention relates to a new therapeutic composition having an anti-blood-platelet aggregation activity and an anti-thrombotic activity.

It is known, since 1976, that the vascular walls contribute primarily to the maintenance of blood platelets in an inactivated condition, through the production of prostacycline, $PGI_2$.

$PGI_2$ is synthesized from arachidonic acid in the cells of the vascular walls. In blood-platelets, this same precursor is converted to prostaglandins $E_2$, $D_2$ and $F_2$ and to thromboxane $A_2$ which is an extremely aggregant metabolite. While functionally antagonistic, both these metabolic routes involve the same intermediates, endoperoxides $PGG_2$ and $PGH_2$.

Figure 1:
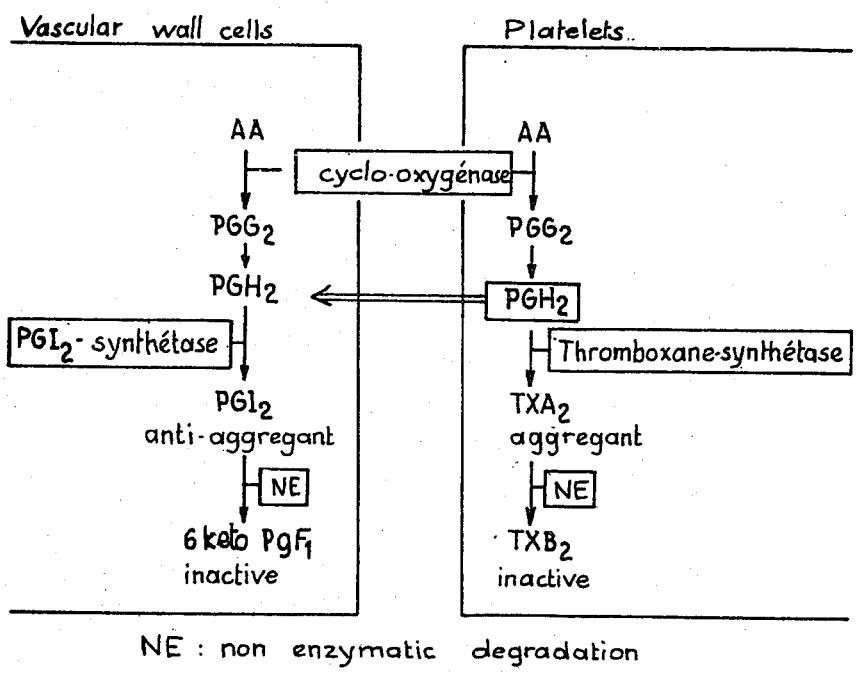
Figure 1:
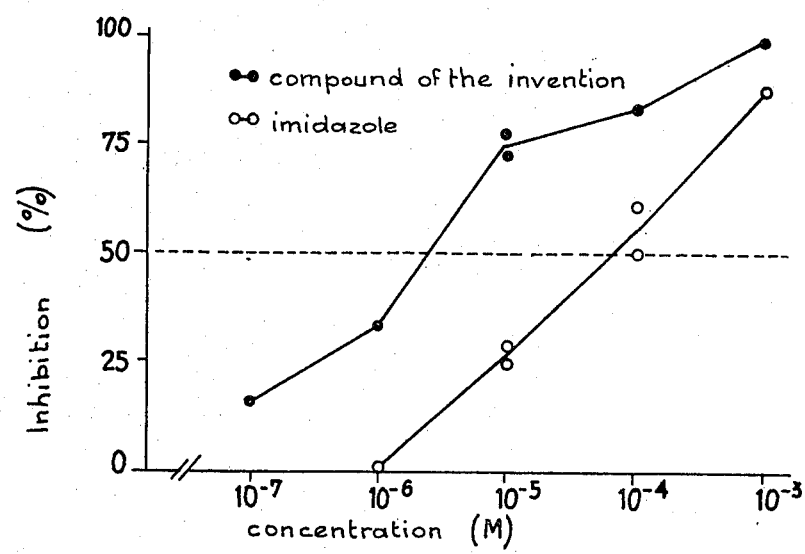

This double synthesis of prostaglandins from arachidonic acid (AA) in the vascular wall cells and in the blood-platelets may be illustrated diagrammatically as shown in FIG. 1.

The metabolism of arachidonic acid to prostaglandins and thromboxanes is inhibited by aspirin as early as the first stage (cyclo-oxygenase). Thus, this material prevents platelet aggregation via thromboxanes but, conversely, by reducing the synthesis of prostacycline by the vascular walls, it increases the susceptibility of the platelets to thrombogenic agents.

It appeared preferable to block thromboxane formation in the blood-platelets in a more downstream position in the metabolic sequence and attempts have been made to inhibit thromboxane synthetase.

Various materials have already been suggested for this purpose, and particularly imidazole (Moncada et al. Prostaglandines 13 611–618, 1977).

Tai and Yuan (Biochem. Biophys. Res. Comm. 80, 236–242, 1978) studied various imidazole derivatives and found that the inhibitory potency was quite substantial in derivatives substituted at 1-position with an alkyl or aryl chain.

The present invention is based on the finding that the compounds having the general formula (I):

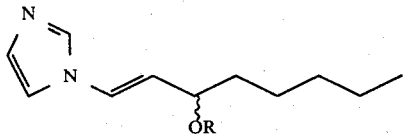

(in which R is hydrogen or an ether or ester residue) and their pharmaceutically acceptable acid addition salts, have a strong specific inhibitory potency on thromboxane synthetase while permitting increased prostacycline $PGI_2$ synthesis.

Pharmacological investigations confirmed that this inhibitory activity was reflected by an anti-blood-platelet aggregation activity and an anti-thrombotic activity.

Therefore, this invention relates to a therapeutic composition having an inhibitory activity on thromboxane synthetase, an anti-blood-platelet aggregation activity and an anti-thrombotic activity, comprising, as active ingredient, a compound of the formula (I) or a pharmaceutically acceptable acid addition salt thereof and a therapeutically acceptable excipient.

The acid addition salts may typically be those formed with hydrohalic, sulfuric, nitric, phosphoric, formic, acetic, fumaric, oxalic, malic, methanesulfonic, lactic, succinic, tartaric, pamoic acids and acidic metal salts such as disodium orthophosphate and monopotassium sulfate.

The esters are typically compounds of the formula (II)

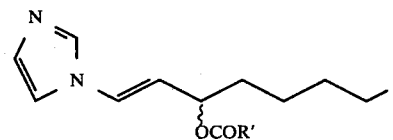

and the ethers are typically compounds of the formula (III):

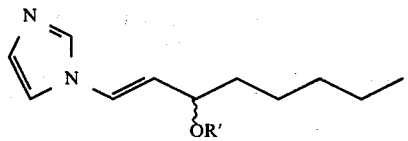

in which formulae R' represents a $C_{1-8}$ alkyl radical, an aryl radical, an aryl ($C_{1-5}$ alkyl)radical or a ($C_{1-5}$ alkyl)aryl radical, the term aryl designating an aromatic hydrocarbon radical having 6–10 carbon atoms, such as a phenyl radical, or a 5–11 membered heteroaromatic radical having one or two heteroatoms selected from nitrogen, oxygen and sulfur atoms, such as pyridyl or thienyl radical.

The compounds of the formula (I) may be used as a racemic mixture or as optical isomers.

(E)-1-(3-hydroxy-octen-1-yl)imidazole (racemic) was described by Pailer and Gutwillinger (Monatshefte für Chemie 108, 653–664, 1977), but there is no mention of any contemplated therapeutic application. The hydrochloride of this racemate (compound A) is a white powder, M.P.=98°–100° C.

The ethers and esters of 1-(3-hydroxy-octen-2-yl)-imidazole are new compounds.

These compounds may be prepared according to known methods, typically by reaction of the corresponding alcohol (compound of the formula (I) in which R=H) with a halo-derivative RX in which R represents an ether or ester residue. Thus, to prepare esters of the formula (II), the corresponding alcohol is reacted with a halide of the formula R'COX in which R' has the above-defined meaning and, to prepare ethers of the formula (III), the corresponding alcohol is reacted with a halo-derivative having the formula R'X in which R' has the above-defined meaning.

The reaction may be effected within a low polar anhydrous solvent such as benzene or tetrahydrofuran, in the presence of an alkaline agent such as triethylamine, anhydrous potassium carbonate or sodium hydride dispersed in oil.

The molar ratio alcohol/halo-derivative/alkaline agent is preferably 1:1.3:1.4 in the reaction mixture.

The reaction is generally effected by heating, and the heating time required for completion of the reaction is about 4–16 hours after introduction of the halo-derivative in the reaction mixture.

The salts are obtained in conventional manner, by action of the corresponding acid on the compounds of the formula (I) dissolved in a solvent such as an alcohol, a ketone or an aliphatic ether.

The following non-limiting Examples illustrate the preparation of the new compounds of this invention.

EXAMPLE 1

(E)-1-(3-hydroxy-octen-1-yl)imidazole nicotinic ester dihydrochloride (E)-1-(3-hydroxy-octen-1-yl)imidazole (0.03 mole) dissolved in benzene (50 ml) is added to a mixture of nicotinoyl chloride (0.04 mole) and triethylamine (0.05 mole) in benzene (100 ml). The reaction mixture is heated to the boiling point for 12 hours. After cooling, the triethyl amine hydrochloride is suction filtered and the benzene solution is washed with water. The organic phase is extracted with dilute hydrochloride acid and the aqueous solution is washed with ethyl ether. The ether solution is dried and the solvent is evaporated off in vacuo.

The nicotinic ester is obtained as an oil, in a yield of 67%.

The dihydrochloride of the above ester is obtained by passing a stream of gaseous hydrochloric acid through an ether solution of the ester. The crude dihydrochloride precipitate is suction filtered and is then recrystallized from methanol-ethyl ether.

The pure (E)-1-(3-hydroxy-octen-1-yl)imidazole nicotinic ester dihydrochloride is obtained as white crystals having a melting point of 145°–148° C.

Spectroscopic properties of the free base
I.R. (film): $\nu = 1720$ cm$^{-1}$, intense C═O band.
N.M.R. (CDCl$_3$): $\delta = 0.42$–2.08 ppm 11H (broad); $\delta = 5.48$ ppm 1H (quartet); $\delta = 5.68$ ppm 1H (quartet, vinyl proton); $\delta = 6.82$–7.18 ppm 3H (broad, 2 imidazole protons, 1 vinyl proton); $\delta = 7.28, 8.18, 8.65, 9.13$ ppm 4H (nicotinic protons).

EXAMPLE 2

(E)-1-(3-hydroxy-octen-1-yl)imidazole 2-pyridyl methyl ether fumarate

Sodium hydride (0.042 mole) dispersed in oil (20%) is added at room temperature to a solution of (E)-1-(3-hydroxy-octen-1-yl)imidazole (0.030 mole) in anhydrous tetrahydrofuran (70 ml). The resulting material is heated at 60° C. for 2 hours and 2-chloromethyl pyridine (0.036 mole) dissolved in anhydrous tetrahydrofuran (30 ml) is then added thereto. The reaction mixture is maintained at 60° C. for 3 hours after completion of the addition. After evaporating off the solvent in vacuo, the residue is triturated with ethyl ether, after which the ether solution is washed with water and is then dried and evaporated in vacuo. The crude ether is obtained as an oil, in a yield of 85%.

It may be purified by column chromatography (silica) with ethyl ether as eluent.

The fumarate of the above ether is prepared by heating at 50° C. for 15 minutes equivalent amounts of fumaric acid and of crude ether in methanol solution.

After evaporating off the methanol in vacuo, the residue is triturated with ethyl ether. The (E)-1-(3-hydroxy-octen-1-yl)imidazole 2-pyridyl methyl ether fumarate precipitate is suction filtered and then recrystallized from ethyl acetate.

The pure salt, obtained in a yield of 62%, occurs as white crystals which melt at 82°–85° C.

Spectroscopic properties of the free base
N.M.R. (CDCl$_3$): $\delta = 0.67$ at 2.00 ppm 11H (broad); $\delta = 3.98$ ppm 1H (quartet); $\delta = 4.65$ ppm 2H (quartet, methylene $\alpha$ to the pyridine nucleus); $\delta = 5.73$ ppm (quartet, vinyl proton); $\delta = 6.77$–7.93 ppm 7H (broad, imidazole protons, 3 pyridinic protons, 1 vinyl proton); $\delta = 8.58$ ppm (1 pyridinic proton).

The characteristics of the compounds of the formula (I) prepared in Examples 1 and 2 and those of other compounds prepared in a similar manner are tabulated in following Table I.

Results of the pharmacological and toxicological investigation effected with the compounds of the formula (I) are given below.

1—Biochemical pharmacology 1.1 Inhibition of platelet thromboxane synthetase

Platelet rich plasma (PRP) is prepared by centrifugation of venous blood at 150 g × 10 min. The platelets are sedimented at 2000 g × 20 min. and washed in a tris-HCl buffer at pH 7.5 (15 mM) containing EDTA (1.5 mM), NaCl, (150 mM) and KCl (5 mM). The platelet pellet is then suspended in a volume of tris-HCl (50 mM) at pH 7.5 corresponding to one-half the original PRP volume. Aliquots of platelet suspension (0.5 ml) are incubated with 1 $\mu$g $^{14}$C-arachidonic acid (specific activity = 50 mCi/mmole) as the Na salt for 10 min. at 37° C. in the presence or the absence of test material. On completion of the reaction, the incubate is cooled to 0°–4° C., made acidic and salted by addition of citric acid and NaCl and then extracted with 2×2 ml ethyl acetate. A PGE$_2$ standard is added to the extract which, after evaporation to dryness, is submitted to a bidimensional chromatography over a thin layer of silica (Merck F 254) in the systems: (1) benzene/dioxan/acetic acid (60:30:3); (2) chloroform/methanol/acetic acid/water (90:8:1:0.8).

TABLE I

| Compound | R | M.P.(°C.) | Yield (%) | Salt formed | M.P.(°C.) | Crystallization solvent |
|---|---|---|---|---|---|---|
| B | —OC-pyridyl | oil | 77 | di-hydrochloride | 145–8 | Methanol-Ether |
| C | —OC-phenyl | oil | 52 | Oxalate | 110–13 | Ethyl acetate-ether |
| D | —OC—CH$_3$ | oil | 92 | Oxalate | 76–8 | Methanol-Ether |
| E | —OC—(CH$_2$)$_4$—CH$_3$ | oil | 50 | Oxalate | 61–2 | Methanol-Ether |

TABLE I-continued

| Compound | R | M.P.(°C.) | Yield (%) | Salt formed | M.P.(°C.) | Crystallization solvent |
|---|---|---|---|---|---|---|
| F | —H$_2$C—C$_6$H$_5$ 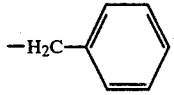 | 66 | 50 | — | — | — |
| G | —H$_2$C—(pyridyl) 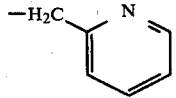 | oil | 67 | Fumarate | 82–5 | Ethyl acetate |

The PGE$_2$ standard is visualized with phosphomolybdic acid in the hot. The radioactivity corresponding to the metabolites of arachidonic acid is measured with a Berthold scanner. The results illustrative in FIG. 2 show that compound A of this invention, just as imidazole, inhibits the formation of thromboxane A$_2$ measured by its stable degradation product, thromboxane. Concomitantly to this inhibition, increasing amounts of PGE$_2$ are formed. This observation indicates that the pharmacological agents tested do not inhibit concomitantly the cyclo-oxygenase.

Table II sets forth results of the determination of the 50% inhibitory concentrations (IC$_{50}$), in moles.

TABLE 2

| Compound | IC$_{50}$ (M) |
|---|---|
| A | 2.5 × 10$^{-6}$ |
| B | 10$^{-6}$ |
| C | 1.5 × 10$^{-6}$ |
| D | 1.5 × 10$^{-6}$ |
| E | 1.5 × 10$^{-6}$ |
| F | 10$^{-6}$ |
| G | 1.5 × 10$^{-6}$ |
| Imidazole | 50 × 10$^{-6}$ |

It is apparent, from a comparison of the IC$_{50}$ that the compounds of the formula (I) are much more active than imidazole under such experimental conditions.

1.2 Use of platelet endoperoxides by the prostacycline-synthetase of vascular microsomes The aorta of a 2.5 kg male rabbit is finely cut, ground in Tris-HCl buffer (50 mM, pH 7.5), and is then homogenized at 0°–4° C. The homogenate is centrifuged at 10000 g×10 minutes. The microsomal pellet is suspended and homogenized in Tris-HCl (50 mM) in an amount of 1.5 mg proteins/ml (the proteins are determined by the method according to Lowry et al.). A human platelet suspension is prepared and incubated as described above, in the presence or the absence of aortal microsomes (100 μg proteins/incubate) and of test material (10$^{-5}$ M). On completion of the reaction, the supernatant is extracted after acidification and chromatographed over a thin silica layer in the organic phase of the system ethyl acetate/2,2,4-trimethylpentane/acetic acid/water (110:50:20:100) in the presence of a 6-keto-PgF$_1$α standard.

The radiochromatograms corresponding to the different incubates are illustrated in FIGS. 3 to 6.

(1) Platelet suspension (FIG. 3): 60% of the extracted radioactivity exhibit a Rf=0.25–0.27 corresponding to thromboxane B$_2$ (TXB$_2$) degradation product of thromboxane A$_2$. Other metabolites, an unidentified polar material, PGD$_2$ and a product having Rf=0.47 are also separated.

(2) Aortal microsomes (FIG. 4): under the experimental conditions described, arachidonic acid (AA) is not metabolized. These results are consistent with those reported by Moncada et al. (Nature, 263, 663–665 (1976)).

(3) Platelet suspension+microsomes (FIG. 5): when platelets are incubated in the presence of aortal microsomes, the metabolic profile is qualitatively modified. A radioactivity peak appears at Rf=0.14 corresponding to 6-keto PgF$_1$α, degradation product of PGI$_2$. This peak, however, represents only 18% of the extracted radioactivity and appears essentially to the detriment of thromboxane B$_2$ (TXB$_2$).

(4) Compound A+platelet suspension+microsomes (FIG. 6): when the preceding incubation is effected in the presence of compound A (0.01 mM), the major portion (65%) of the arachidonic acid is metabolized to 6-keto-PgF$_1$α, while the radioactivity corresponding to thromboxane B$_2$ represents only 20%. There is concomitantly noted an almost complete suppression of the lesser polar materials.

It is apparent from the above results that, on the one hand, compound A inhibits strongly the synthesis of thromboxane A$_2$, which is an aggregant, and, on the other hand, that it promotes in such a system the synthesis of prostacycline PGI$_2$ which is itself an anti-aggregant.

2—Functional pharmacology 2.1 Ex vivo platelet aggregation in rabbits

Groups of 3 male rabbits are treated subcutaneously for two consecutive days and their plasma is taken two hrs after the second administration. Arachidonic acid-induced (2 mM) platelet aggregation is measured by the turbidimetric method according to Born.

The analysis of the aggregation curves reported in Table III shows that compound A according to this invention, at a dosage of 5 mg/kg, produces a very substantial decrease of arachidonic acid-induced platelet aggregation in rabbits.

TABLE III

| | Ex-vivo platelet aggregation in rabbits | | |
|---|---|---|---|
| Treatment | Aggregation rate (⊕)[1] | Maximum (⊕)[2] | Deaggregation rate (⊕)[1] |
| Controls | 56 | 40 | 5 |
| Compound A (5mg × kg$^{-1}$) | 32 | 28 | 3 |

⊕ means for groups of 3 animals each
[1] arbitrary units
[2] % of maximum aggregation 2.2 Bleeding time (ear) in rabbits Groups of 3 male rabbits are treated subcutaneously with the test materials. Bleeding time (BT) is determined just before, and then 2 hours and 4 hours after their administration according to a standard procedure, by a "blind" acting experimenter.

The bleeding time measures are reported in Table IV. The animals treated with a single dose (5 mg/kg) of Compound A according to this invention exhibit a BT extended by a factor of two at time 2 hours after treatment; this extension is highly significant and is found to continue at time 4 hours.

TABLE IV

| | Bleeding time (ear) in rabbits | | |
|---|---|---|---|
| | Bleeding time (seconds)⊕ | | |
| Treatment | Time 0 | Time 2 hours | Time 4 hours |
| Controls | 70 ± 23 | 85 ± 31 | 87 ± 29 |
| Compound A (5mg × kg$^{-1}$) | 80 ± 27 | 165 ± 38 | 102 ± 19 |

⊕ mean value ± standard deviation for groups of three animals each

3—Inhibition of collagen-induced platelet aggregation and determination of the inhibition of thromboxane synthesis.

Venous blood sampled from volunteers is collected on sodium citrate. The platelet rich plasma (PRP) is prepared by centrifugation at 150 g×10 min.

300 μl PRP are incubated in siliconized tubes in an aggregometer in the presence or the absence of test material dissolved in 100 μl buffer, and 20 μg collagen (Stago) are then added. Platelet aggregation is recorded by the decrease of the optical density. After 4 minutes, an acetylsalicylic acid solution (2×10$^{-4}$ M final) is added to block the synthesis of prostanoids, and thromboxane B$_2$ is titrated in the liquid phase of the incubate by radioimmunoassay. The results obtained are given in Table V.

TABLE V

| Incubate | Aggregation (%) | T × B$_2$ formed (pmole/ml PRP) |
|---|---|---|
| Control | 100 | 900 |
| Compound B (10$^{-6}$M) | 50 | 400 |
| Compound B (10$^{-5}$M) | 7 | 100 |

4—Acute toxicity

The compounds of the formula (I) have a toxicity that appears only at dosages highly superior to the pharmacologically active dosages. In Table VI are set forth results of the determination of the LD$_{50}$ of Compound A on intraperitoneal administration to Wistar rats and Swiss mice.

TABLE VI

| LD$_{50}$ of Compound A on intraperitoneal administration to rats and mice | | |
|---|---|---|
| Species | Sex | LD$_{50}$⊕(mg × kg$^{-1}$) |
| Rats | M | 270 ± 12 |
| " | F | 250 ± 16 |
| Mice | M | 166 ± 7 |
| " | F | 164 ± 6 |

⊕ mean value ± 5% confidence interval

The therapeutic compositions of this invention are typically applicable for the treatment and prevention of thromboses, particularly for thromboses in diabetic patients, and for retinal thromboses, and also for the treatment of diabetic retinopathy.

The therapeutic compositions of this invention are administrable to humans by the oral route (as tablets or capsules) or by the parenteral route (as aqueous solutions, typically for intravenous infusion).

When formulated in unit dosage form for oral administration, they may contain 20-100 mg active ingredient.

The dialy dosage regimen may vary from 80 mg to 400 mg active ingredient.

An example of an administrable composition is given hereinunder

| Capsule: | Compound B | 50 mg |
|---|---|---|
| | Lactose | 250 mg |
| | Talc | 5 mg |
| | Magnesium stearate | 2 mg |

Having now described our invention what we claim as new and desire to secure by Letters Patent is:

1. A compound of the formula (III):

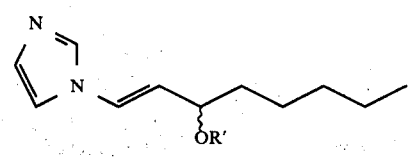

(III)

in which R' represents a C$_{1-8}$ alkyl radical, an aryl radical, an aryl(C$_{1-5}$alkyl) or (C$_{1-5}$alkyl)aryl radical, the term "aryl" designating an aromatic hydrocarbon radical having 6-10 carbon atoms or a pharmaceutically acceptable acid addition salt thereof.

2. A composition having an inhibitory activity on thromboxane synthetase containing an effective amount of a compound of the formula

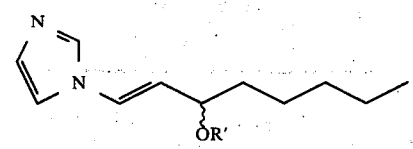

(III)

in which R' represents a C$_{1-8}$alkyl radical, an aryl radical, an aryl (C$_{1-5}$alkyl) or (C$_{1-5}$alkyl) aryl radical, the term "aryl" designating a non-heterocyclic aromatic hydrocarbon radical containing 6-10 carbon atoms, and a pharmaceutically acceptable acid addition salt thereof, in admixture with a therapeutically acceptable excipient.

3. A process for the treatment and prevention of thromboses which comprises administering to a human in need thereof an effective amount of a compound selected from the group consisting of a coompound of the formula

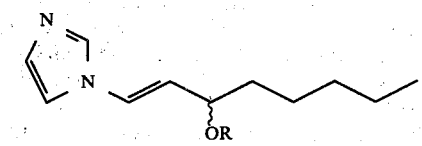

(I)

in which R represents a hydrogen atom and a pharmaceutically acceptable acid addition salt thereof.

4. A process for the treatment and prevention of thromboses which comprises administering to a human in need thereof an effective amount of a compound selected from the group consisting of a compound of the formula

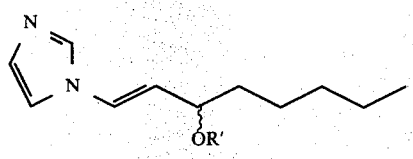

(III)

in which R' represents a $C_{1-8}$ alkyl radical, an aryl radical, an aryl ($C_{1-5}$ alkyl) or ($C_{1-5}$ alkyl) aryl radical, the term "aryl" designating a non-heterocyclic aromatic hydrocarbon radical containing 6–10 carbon atoms, and a pharmaceutically acceptable acid addition salt thereof, in admixture with a therapeutically acceptable excipient.

5. A composition as claimed in claim 2, in which said effective amount is 20–100 mg and said composition is in unit dosage form for oral administration.

6. A process as claimed in claim 3, said effective amount being 80–400 mg per day.

7. A process as claimed in claim 4, said effective amount being 80–400 mg per day.

8. A therapeutic composition having anti-blood platelet aggregating activity containing an effective amount of a compound selected from the group consisting of a compound of the formula

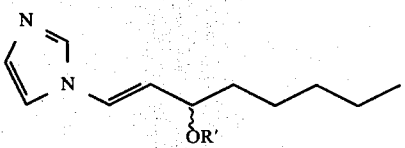

(III)

in which R' represents a $C_{1-8}$ alkyl radical, an aryl radical, an aryl ($C_{1-5}$ alkyl) or ($C_{1-5}$ alkyl) aryl radical, the term "aryl" designating a non-heterocyclic aromatic hydrocarbon radical containing 6–10 carbon atoms, and a pharmaceutically acceptable acid addition salt thereof, in admixture with a therapeutically acceptable excipient.

9. A process for the treatment and prevention of thromboses which comprises administering to a human in need thereof an effective amount of a compound selected from the group consisting of a compound of the formula (II)

in which R' represents a $C_{1-8}$ alkyl radical, an aryl radical, an aryl ($C_{1-5}$ alkyl) or ($C_{1-5}$ alkyl) aryl radical, the term "aryl" designating a non-heterocyclic aromatic hydrocarbon radical having 6–10 carbon atoms, and a pharmaceutically acceptable addition salt thereof, in admixture with a therapeutically acceptable excipient.

10. A composition as claimed in claim 8, in which said effective amount is 20–100 mg and said composition is in unit dosage form for oral administration.

11. A process as claimed in claim 9, said effective amount being 80–400 mg per day.

* * * * *